(12) United States Patent
Brown et al.

(10) Patent No.: US 11,076,995 B2
(45) Date of Patent: Aug. 3, 2021

(54) COLD-DRAWN POLYOLEFIN COPOLYMERS CORD FOR EARPLUG

(71) Applicant: 3M INNOVATIVE PROPERTIES COMPANY, St. Paul, MN (US)

(72) Inventors: James D. Brown, Bloomington, IN (US); Feng Cai, Carmel, IN (US); Robert C. Coffin, Plainfield, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/643,153

(22) PCT Filed: Aug. 30, 2018

(86) PCT No.: PCT/IB2018/056646
§ 371 (c)(1),
(2) Date: Feb. 28, 2020

(87) PCT Pub. No.: WO2019/043625
PCT Pub. Date: Mar. 7, 2019

(65) Prior Publication Data
US 2020/0179173 A1   Jun. 11, 2020

Related U.S. Application Data

(60) Provisional application No. 62/553,639, filed on Sep. 1, 2017.

(51) Int. Cl.
*B29C 55/00*  (2006.01)
*B29K 23/00*  (2006.01)
(Continued)

(52) U.S. Cl.
CPC .............. *A61F 11/12* (2013.01); *B29C 55/00* (2013.01); *B29C 55/005* (2013.01);
(Continued)

(58) Field of Classification Search
CPC ......... B29L 2031/768; B29L 2223/083; B29L 2423/083; B29L 2623/083; A61F 11/06;
(Continued)

(56) References Cited

U.S. PATENT DOCUMENTS 4,193,396 A * 3/1980 Wacker .................. B29C 65/08
128/864
4,219,018 A * 8/1980 Draper, Jr. .............. A61F 11/08
128/864
(Continued)

FOREIGN PATENT DOCUMENTS

CN         101661143         3/2010
CN         202821828         3/2013
(Continued)

OTHER PUBLICATIONS

Ethylene Vinyl Acetate Properties, Omnexus, Apr. 20, 2017 table 1 https //omnexus specialchem.com/ selection-guide/ethylene vinyl acetate/ properties of eva.
(Continued)

*Primary Examiner* — Jeffrey M Wollschlager
(74) *Attorney, Agent, or Firm* — Katherine M. Scholz

(57) ABSTRACT

An earplug assembly and method of forming the same is described. The method includes uniaxially stretching a cord formed of copolymer including ethylene segments and vinyl acetate segments to form a cold-drawn cord. The cold drawn cord has an elongation to break of 250% or less. The method then includes fixing the cold drawn cord to an earplug.

11 Claims, 2 Drawing Sheets

(51) Int. Cl.
  *B29L 31/00* (2006.01)
  *A61F 11/12* (2006.01)
(52) U.S. Cl.
  CPC .............................. *B29K 2023/083* (2013.01); *B29K 2995/0077* (2013.01); *B29L 2031/768* (2013.01)
(58) Field of Classification Search
  CPC .... A61F 11/08; A61F 2011/085; A61F 11/10; A61F 11/12; A61F 11/00; B29K 2023/083; B29K 2223/083; B29K 2423/083; B29K 2623/083; B29K 2823/083; B29K 2995/0077; B29C 55/005; B29C 55/00; B29C 48/0018; B29C 48/05; B29C 48/06
  USPC .......................................... 128/864, 865, 867
  See application file for complete search history.

(56) References Cited

U.S. PATENT DOCUMENTS

| | | | | |
|---|---|---|---|---|
| 4,253,452 A * | 3/1981 | Powers | ................... | A61F 11/08 128/864 |
| 4,293,355 A * | 10/1981 | Wacker | ................... | A61F 11/08 128/864 |
| 4,314,553 A | 2/1982 | Westerdal | | |
| 4,481,158 A | 11/1984 | Georlette | | |
| 4,500,677 A * | 2/1985 | Maruhashi | ............. | C08L 29/04 525/57 |
| 4,555,313 A | 11/1985 | Duchane | | |
| 4,806,186 A * | 2/1989 | Sirkin | ..................... | A61F 11/08 156/80 |
| 5,249,309 A | 10/1993 | Berg | | |
| 5,290,635 A * | 3/1994 | Matsumura | ........... | B29C 55/005 428/516 |
| 5,509,355 A | 4/1996 | Stewart | | |
| 5,541,677 A | 7/1996 | Huhtala | | |
| 5,581,821 A | 10/1996 | Nakano | | |
| 5,668,354 A * | 9/1997 | Falco | ..................... | A61F 11/12 128/864 |
| 5,711,313 A | 1/1998 | Fleming | | |
| 5,799,658 A * | 9/1998 | Falco | ..................... | A61F 11/14 128/864 |
| 5,806,506 A | 9/1998 | Kitamura | | |
| 5,811,742 A | 9/1998 | Leight | | |
| 6,340,227 B1 | 1/2002 | Solberg | | |
| 6,440,339 B1 * | 8/2002 | Magidson | ............... | A61F 11/08 264/157 |
| 7,659,219 B2 | 2/2010 | Biran | | |
| 9,650,508 B2 * | 5/2017 | Oriani | ................. | C08L 23/0853 |
| 2002/0124851 A1 | 9/2002 | Knauer | | |
| 2004/0079579 A1 * | 4/2004 | Barwacz | ................. | A61F 11/12 181/135 |
| 2005/0229938 A1 * | 10/2005 | Jenkins, Jr. | ............. | A61F 11/08 128/854 |
| 2005/0230181 A1 * | 10/2005 | Woo | ........................ | A61F 11/12 181/135 |
| 2007/0086599 A1 | 4/2007 | Wilmink | | |
| 2007/0227546 A1 | 10/2007 | Schumaier | | |
| 2012/0073583 A1 | 3/2012 | Turdjian | | |
| 2012/0272974 A1 | 11/2012 | Magidson | | |
| 2013/0014768 A1 | 1/2013 | Vaarbroe | | |
| 2015/0000016 A1 * | 1/2015 | Crawford | ............... | G02C 11/00 2/423 |
| 2015/0139470 A1 * | 5/2015 | Ely | ......................... | A61F 11/12 381/374 |
| 2015/0140246 A1 * | 5/2015 | Oriani | ................. | C08L 23/0853 428/36.9 |
| 2017/0079845 A1 * | 3/2017 | Cai | ......................... | A61F 11/08 |
| 2020/0297539 A1 * | 9/2020 | Cai | ......................... | A61F 11/08 |

FOREIGN PATENT DOCUMENTS

| | | | |
|---|---|---|---|
| JP | 55051864 | * | 4/1980 |
| WO | WO 2001/16228 | | 3/2001 |

OTHER PUBLICATIONS

International Search report for PCT International Application No. PCT/IB18/56646 dated Dec. 7, 2018, 2 pages.

*Declaration Technique of Import and Export Goods of Customs of PRC*, pp. 252-255, 12.5.4 Ethylene Vinylacetate Copolymer, Edited by the Department of Tariff Collection, General Administration of Customs of PRC.

Extended EP Search Report, EP 18849910.7, dated Apr. 21, 2021 (8 pages).

* cited by examiner

COLD-DRAWN POLYOLEFIN COPOLYMERS CORD FOR EARPLUG

CROSS REFERENCE TO RELATED APPLICATIONS

This application is a national stage filing under 35 U.S.C. 371 of PCT/IB2018/056646, filed Aug. 30, 2018, which claims the benefit of U.S. Provisional Application No. 62/553,639, filed Sep. 1, 2017, the disclosure of which is incorporated by reference in its/their entirety herein.

BACKGROUND

The use of hearing protective and noise attenuating devices are well known, and various types of devices have been considered. Such devices include earplugs and semi-aural devices partially or completely constructed of foam or rubber materials that are inserted into, or placed over, the ear canal of a user to physically obstruct the passage of sound waves into the inner ear.

Compressible or "roll-down" type earplugs generally comprise a compressible, resilient body portion and may be made of suitable slow recovery foam materials. The earplug may be inserted into the ear canal of a user by first rolling it between fingers to compress the body portion, then pushing the body portion into the ear canal, and subsequently allowing the body portion to expand to fill the ear canal.

Push-to-fit type earplugs have also been considered, and may include a compressible attenuating portion and a stiff portion that extends from the attenuating portion. To insert a push-to-fit type earplug, the user grasps the stiff portion and pushes the attenuating portion into the ear canal with an appropriate level of force. The attenuating portion compresses as it is accommodated in the ear canal. Push-to-fit earplugs may allow the earplug to be quickly and easily inserted in an ear canal, and may promote hygiene by minimizing contact with the attenuating portion of the earplug prior to insertion.

Earplugs often include a cord or tether that attaches a pair of earplugs and extends therebetween. The tether or cord allows a user to hang the earplugs around their neck or elsewhere when the earplugs are not being used. Also, the cord or tether permanently relates a pair of earplugs and prevents against loss thereof. In the context of other tethered personal protective devices, the provided tether oftentimes performs these same functions.

Conventional cords or tethers are commonly designed so that the cord or tether may be permanently attached to the earplugs and more specifically, each end of the cord or tether may be permanently attached to the ends of the earplugs. In the case of roll-down type earplugs, a cord is attached to one end of the resilient body. Push-to-fit stem type earplugs generally have the cord attached at the exposed portion of the stem. Tethers or cords may be attached to the various types of earplugs, for example, by ultrasonic welding or by adhesive bonding.

SUMMARY

The present disclosure relates to cold drawn polyolefin copolymers cord for earplugs. In particular, the present disclosure relates to cold drawn ethylene vinyl acetate cord for earplugs.

Cold drawing ethylene vinyl acetate cord increases its elastic modulus to provide a less "springy" or less elastic cord when fixed to one or more earplugs. Cold drawing ethylene vinyl acetate cord may reduce or eliminate undesirable plastic or elastic deformation and improve material handling during earplug manufacture.

In one aspect, a method includes uniaxially stretching a cord formed of copolymer including ethylene segments and vinyl acetate segments to form a cold-drawn cord. The cold drawn cord has an elongation to break of 250% or less. The method then includes fixing the cold drawn cord to an earplug.

In another aspect, an earplug assembly includes an earplug and a flexible cord extending from a first cord end to a second cord end and the first cord end fixed to the earplug. The flexible cord formed of copolymer comprising ethylene segments and vinyl acetate segments. The flexible cord has an elastic modulus of 10 MPa or greater at 100% elongation.

These and various other features and advantages will be apparent from a reading of the following detailed description. The above summary is not intended to describe each embodiment or every implementation of the earplugs and methods of manufacturing earplugs as described herein. Rather, a more complete understanding of the invention will become apparent and appreciated by reference to the following Detailed Description and claims in view of the accompanying figures of the drawing.

DETAILED DESCRIPTION

Figure 1:
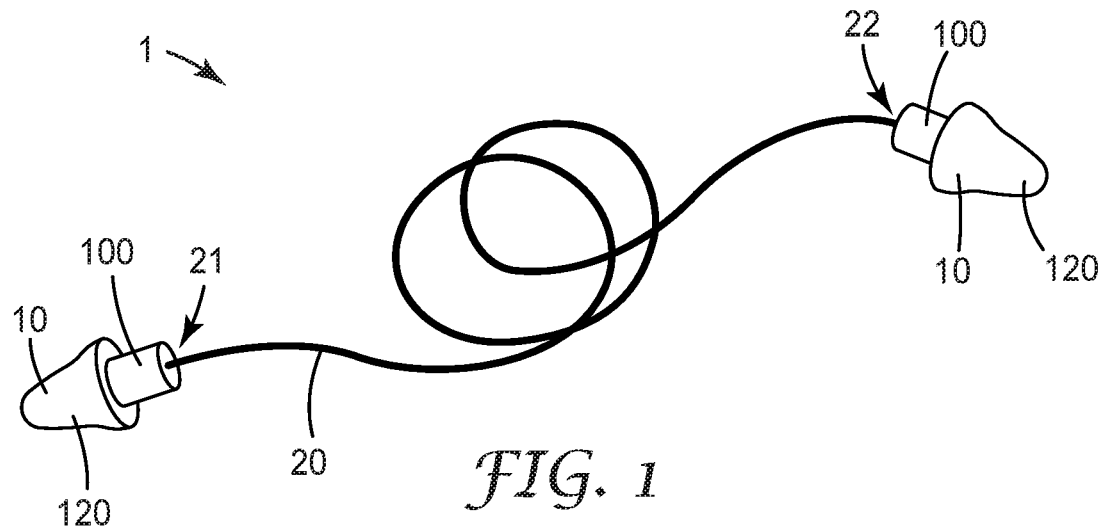
FIG. 1 is a schematic diagram of an illustrative earplug assembly.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

"Copolymer" refers to, unless otherwise indicated, polymers formed from two or more monomers or comonomers, including terpolymers, for example.

"Room Temperature" refers to typical environmental room temperatures such as a range from 20 to 30 degrees Celsius, or about 25 degrees Celsius, and 1 atmosphere.

"Thermally bonded" refers to a state in which molecules of two materials or surfaces have diffused into the material or surface of the other when in a molten phase such that a bond is formed. Chemical bonding is absent or does not provide the primary source of bonding between thermally bonded materials or surfaces.

The present disclosure relates to cold drawn polyolefin copolymers cord for earplugs. In particular, the present disclosure relates to cold drawn ethylene vinyl acetate cord for earplugs. Cold drawing ethylene vinyl acetate cord increases its elastic modulus to provide a less "springy" or less elastic cord when fixed to one or more earplugs. Cold drawing ethylene vinyl acetate cord may reduce or eliminate undesirable plastic or elastic deformation of the cold drawn cord and improve material handling during earplug manufacture. The cold drawn ethylene vinyl acetate cord may be formed by uniaxial stretching an ethylene vinyl acetate cord at least 250% or at least 300% to form the cold drawn ethylene vinyl acetate cord. The cold drawn ethylene vinyl acetate cord may have an elongation to break of less than 300%, or less than 200%. The cold drawn ethylene vinyl acetate cord may have an elastic modulus of 10 MPa or greater, or 20 MPa or greater, all at 100% elongation. Prior to cold drawing, the ethylene vinyl acetate cord may have an elastic modulus of less than 7 MPa or less than 6 MPa. The cold drawn ethylene vinyl acetate cord may then be fixed to an earplug to form the earplug assembly. While the present disclosure is not so limited, an appreciation of various aspects of the disclosure will be gained through a discussion of the examples provided below.

FIG. 1 is a schematic diagram of an illustrative earplug 1 assembly. According to at least some embodiments, the earplug assembly 1 includes two earplugs 10 connected by a cord 20. While this disclosure discusses assemblies including two earplugs, an assembly with only a single earplug attached to a cord could be imagined and are considered to be within the scope of this disclosure.

Various types of earplugs can be used as part of the earplug assembly 1. For example, the earplugs may include a stem or central core, and may additionally include a sound-attenuating body. Alternatively, the earplug stem itself may function as the sound-attenuating body. The earplug assembly 1 shown includes earplugs 10 with a stem 100 and a sound-attenuating body 120.

In the embodiment shown, a sound attenuating body 120 is attached to the stem 100. Generally, the sound-attenuating body 120 may be made of the same material as the stem 100, or a different material. The sound-attenuating body 120 may be made of a compressible material (for example, a foam or an elastomer) that may be inserted into the ear canal of the user. The stem 100 may be more rigid than the sound-attenuating body 120. The sound-attenuating body 120 may be formed of a foamed material and the stem 100 may be formed of a material that is denser than the foamed material of the sound-attenuating body 120, or not foamed. The stem 100 may be at least 1.2 times, or at least 1.5 times, or at least 2 times denser than the foamed material of the sound-attenuating body 120.

The cord 20 has a first cord end 21 and a second cord end 22, and a length extending between the first and second cord ends 21, 22. The length of the cord is not limiting, and any useful cord length can be used. Typical cord lengths vary from about 12 to about 30 inches. According to an embodiment, the first and second cord ends 21, 22 are thermally bonded to the stems of the earplugs 10 of the assembly 1. In some embodiments, the attachment is free of adhesives, or if an adhesive is used, it does not provide the primary mechanism of adhesion between the cord and the earplugs.

The stem 100 may be formed from a first material that may include suitable thermoplastic materials. For example, the first material may include polyolefins, such as polypropylene (PP) or polyethylene (PE), polyethylene terephthalate (PET), polybutylene terephthalate (PBT), poly(methyl methacrylate) (PMMA), acrylonitrile butadiene styrene (ABS), polyamide (nylon), polylactic acid, polypropylene, polycarbonate, polyether sulfone (PES), polyoxymethylene (POM), polyether ether ketone (PEEK), polyphenylene oxide (PPO), polyphenylene sulfide (PPS), polystyrene (PS), polyvinyl chloride (PVC), and mixtures and alloys thereof. In certain embodiments, the first material is polypropylene, polyethylene terephthalate, polybutylene terephthalate, nylon, polycarbonate, or a mixture or alloy thereof. One particularly useful first material is polypropylene. The first material may be free of PVC.

The cord 20 is formed of a copolymer comprising ethylene segments and vinyl acetate segments. The cord 20 may be formed of a copolymer referred to as ethylene vinyl acetate or EVA. The cord 20 may be formed of a copolymer having from 90 to 60% wt ethylene segments and from 10 to 40 wt % vinyl acetate segments. The cord 20 may be formed of a copolymer having from 80 to 70% wt ethylene segments and from 20 to 30 wt % vinyl acetate segments. Illustrative EVA is commercially available under the trade designation Ateva series (9 to 40% VA) from Celanese Corp.

The cord material may be extruded prior to cold-drawing. The EVA cord may be formed by extrusion prior to cold-drawing. The cord 20 may be formed of at least 90% EVA material, or at least 95% EVA material, or 99% EVA material, or 100% EVA material. The thermoplastic or polymer material forming the cord 20 may be formed of at least 90% EVA material, or at least 95% EVA material, or 99% EVA material, or 100% EVA material.

EVA is a thermoplastic polyolefin copolymer. The advantages of EVA for cord application include low cost, flexible, good hot adhesion, ease of extrusion and a smooth surface. However, EVA extrudate is easily plastically deformed (too stretchy), which is undesirable for the material assembly and cording automation.

To overcome this stretchy property of the as extruded EVA, the EVA cord may be uniaxial stretched or drawn at room temperature or any temperature below a melt temperature of the extruded EVA, or at least 50 degrees Celsius below a melt temperature of the extruded EVA, or at least 100 degrees Celsius below a melt temperature of the extruded EVA, or at least 150 degrees Celsius below a melt temperature of the extruded EVA, or at least 200 degrees Celsius below a melt temperature of the extruded EVA, (cold drawing process). The EVA cold drawing process creates a polymer chain-orientation morphology along the EVA cord axial direction, which leads to greatly reduced susceptibility to plastic deformation. Cold drawing the EVA cord can be carried out by simply stretching the extruded EVA rope between two sets of rollers. The drawing may occur between feed rollers (slower speed) and take-up rollers (faster speed) at room temperature or any temperature below a melt temperature of the extruded EVA, or at least 50 degrees Celsius below a melt temperature of the extruded EVA, or at least 100 degrees Celsius below a melt temperature of the extruded EVA, or at least 200 degrees Celsius below a melt temperature of the extruded EVA, (cold drawing process). The EVA rope may be uniaxial stretched or drawn at least 200%, or at least 250%, or at least 300%, or at least 400%, forming the cold-drawn cord.

The cold drawn EVA cord may have an elongation to break of 300% or less 250% or less, or 200% or less. The cold drawn EVA cord may have an elastic modulus that is at least 1.2 times, or at least 1.5 times, or at least 2 times, or at least 2.5 times, or at least 3 times, greater than the elastic modulus of the EVA rope prior to cold drawing. The cold drawn EVA cord may have an elastic modulus of 10 MPa or greater, or 15 MPa or greater, or 20 MPa or greater, or 25 MPa or greater, all at 100% elongation. The EVA rope, prior to cold drawing, may have an elastic modulus of 7 MPa or less, or 6.5 MPa or less, or 6 MPa or less, all at 100% elongation.

Cold drawing the EVA rope may reduce a diameter of the rope when forming the cord drawn cord. The EVA rope has an initial diameter and the cold-drawn cord has a cold-drawn diameter in a range from 40% to 80% of the initial diameter. For example, the EVA rope may have an initial diameter of about 2 mm and the cold-drawn cord then has a cold-drawn diameter in a range from 0.8 to 1.6 mm, or about 1.2 mm.

The earplug assembly 1 includes an earplug 10, and a flexible cord 20 extending from a first cord end 21 to a second cord end 22. The first cord end 21 is fixed to the earplug 10. The flexible cord 20 is formed of copolymer having ethylene segments and vinyl acetate segments, as described above. The flexible cord 20 has an elastic modulus of 10 MPa or greater at 100% elongation, as described above.

The earplug assembly 1 may include a second earplug 10 fixed to the second cord end 22. The flexible cord 20 may be uniaxially orientated at least 200%, or at least 250%, or at least 300%, or at least 400%. The flexible cord 20 may be thermally bonded to the earplug 10. The flexible cord 20 may be thermally bonded to the earplug 10 stem 100. The flexible cord 20 may be thermally bonded to the earplug 10 stem 100 formed of polypropylene, for example.

Figure 2:
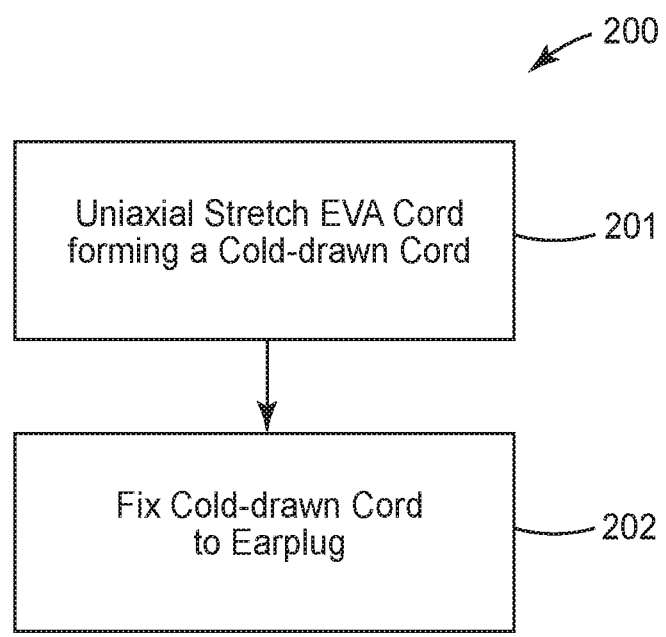
FIG. 2 is a schematic flow diagram of an illustrative cold drawing.

FIG. 2 is a schematic flow diagram 200 of an illustrative cold drawing method. The method includes uniaxially stretching, (step 201) a cord formed of copolymer comprising ethylene segments and vinyl acetate segments to form a cold-drawn cord, the cold drawn cord having an elongation to break of 250% or less, and fixing the cold drawn cord to an earplug (step 202).

The method may further include fixing the cold drawn cord to a second earplug to form an earplug assembly.

EXEMPLARY EMBODIMENTS

Embodiment 1 is a method comprising: uniaxially stretching a cord formed of copolymer comprising ethylene segments and vinyl acetate segments to form a cold-drawn cord, the cold drawn cord having an elongation to break of 250% or less; and fixing the cold drawn cord to an earplug.

Embodiment 2 is a method according to embodiment 1, wherein the cold drawn cord has an elongation to break of 200% or less.

Embodiment 3 is a method according to embodiment 1 or 2, wherein the uniaxially stretching step comprises uniaxially stretching the cord at least 250%, or at least 300%, or at least 350%, or at least 400%.

Embodiment 4 is a method according to any of the preceding embodiments, wherein the cold drawn cord has an elastic modulus of 10 MPa or greater at 100% elongation, or 15 MPa or greater at 100% elongation.

Embodiment 5 is a method according to any of the preceding embodiments, wherein the cold drawn cord has an elastic modulus of 20 MPa or greater at 100% elongation, or 25 MPa or greater at 100% elongation.

Embodiment 6 is a method according to any of the preceding embodiments, wherein the cord has an elastic modulus of 7 MPa or less at 100% elongation, or 6.5 MPa or less at 100% elongation, or 6 MPa or less at 100% elongation.

Embodiment 7 is a method according to any of the preceding embodiments, wherein the uniaxially stretching step comprises uniaxially stretching the cord having an initial diameter to a cold-drawn cord having a cold-drawn diameter in a range from 40% to 80% of the initial diameter.

Embodiment 8 is a method according to any of the preceding embodiments, wherein cold drawn cord has a uniform diameter in a range from 0.08 to 1.6 mm, or from 1 to 1.2 mm.

Embodiment 9 is a method according to any of the preceding embodiments, further comprising fixing the cold drawn cord to a second earplug.

Embodiment 10 is a method according to any of the preceding embodiments, wherein the fixing step comprises fixing the cold drawn cord to a portion of the earplug formed of polypropylene.

Embodiment 11 is a method according to any of the preceding embodiments, wherein the copolymer comprises from 80 to 70% wt ethylene segments and from 20 to 30 wt % vinyl acetate segments, or the copolymer comprises from 90 to 60% wt ethylene segments and from 10 to 40 wt % vinyl acetate segments.

Embodiment 12 is an earplug assembly that may be formed by the method of the preceding embodiments.

Embodiment 13 is an earplug assembly that comprises an earplug, and a flexible cord extending from a first cord end to a second cord end and the first cord end fixed to the earplug, the flexible cord formed of copolymer comprising ethylene segments and vinyl acetate segments, and the flexible cord having an elastic modulus of 10 MPa or greater at 100% elongation.

Embodiment 14 is an earplug assembly according to embodiment 13, wherein the flexible cord has an elongation to break of less than 250%, or less than 200%.

Embodiment 15 is an earplug assembly according to any of embodiments 13 to 14, further comprising a second earplug fixed to the second cord end.

Embodiment 16 is an earplug assembly according to any of embodiments 13 to 15, wherein the flexible cord has an elastic modulus of 15 MPa or greater at 100% elongation, or 20 MPa or greater at 100% elongation, or 25 MPa or greater at 100% elongation.

Embodiment 17 is an earplug assembly according to any of embodiments 13 to 16, wherein the flexible cord has a uniform diameter in a range from 0.8 to 1.6 mm, or from 1 to 1.2 mm.

Embodiment 18 is an earplug assembly according to any of embodiments 13 to 17, wherein the flexible cord is uniaxially orientated.

Embodiment 19 is an earplug assembly according to any of embodiments 13 to 18, wherein the flexible cord is thermally bonded to the earplug.

Embodiment 20 is an earplug assembly according to any of embodiments 13 to 19, wherein the first cord end is fixed to a portion of the earplug formed of polypropylene.

Embodiment 21 is an earplug assembly according to any of embodiments 13 to 20, wherein the copolymer comprises from 80 to 70% wt ethylene segments and from 20 to 30 wt % vinyl acetate segments, or the copolymer comprises from 90 to 60% wt ethylene segments and from 10 to 40 wt % vinyl acetate segments.

Objects and advantages of this disclosure are further illustrated by the following examples, but the particular materials and amounts thereof recited in these examples, as well as other conditions and details, should not be construed to unduly limit this disclosure.

EXAMPLES

Test Methods

The parameter of stretchability (or ease of stretching), was determined by carrying out the consecutive testing steps listed below using an Instron 5967 Universal testing instrument. An EVA cord sample was cut to an initial length. The initial length and diameter of the EVA cord sample was measured and recorded. The EVA cord sample was placed in the Instron testing instrument by attaching the two instrument clamps to the EVA cord sample. The instrument clamps were spaced by a clamping distance of 50.8 mm, and the location of the clamps were marked on the EVA cord sample. The initial clamping distance of 50.8 mm was designated as the original length Lo for all samples tested. All length measurements were subsequently made with reference to the distance between the two clamp markings on the EVA cord sample.

The testing instrument was operated to subject the EVA cord sample to a stretching or tensile force at room temperature (23° C., 50% RH) at a constant rate (e.g., 300%/minute). The EVA cord sample was stretched to a predetermined length at the constant rate. The predetermined length selected for the EVA cord sample was determined by referencing an expected elongation at break for the material of the EVA cord sample. The EVA cord sample was held by the testing instrument at the predetermined length for 3 minutes, and the predetermined length (LMAX) was recorded. Following the 3 minutes holding period, the testing instrument was operated to return the clamps to their original position. A load applied to the EVA cord sample at 100% elongation as reported by the Instron testing instrument was recorded.

Example 1

Figure 3:
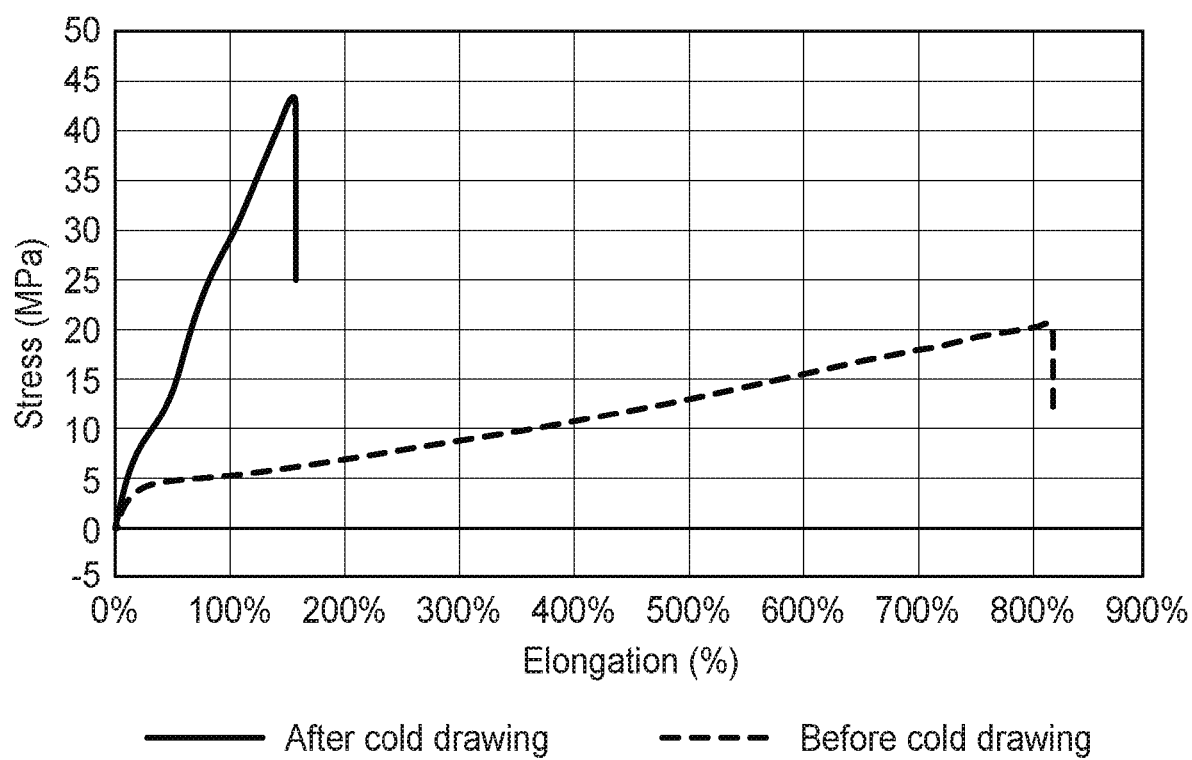
FIG. 3 is a graph illustrating cold drawing effect on elastic modulus of an ethylene vinyl acetate cord.

A rope of ethylene vinyl acetate (Ateva 2810A series (28% VA) from Celanese Corp. having a melt temperature of about 210 degrees Celsius) having a diameter of about 2 mm was tested as described above. FIG. 3 is a graph illustrating cold drawing effect on elastic modulus of an ethylene vinyl acetate cord.

The rope of ethylene vinyl acetate was elongated to break and a curve was recorded (before cold drawing) at the graph of FIG. 3. The modulus at 100% elongation was about 5.2 MPa with an elongation to break of about 800% and a maximum elastic modulus of about 20 MPa at break.

The rope of ethylene vinyl acetate was elongated to about 400% to form the cold-drawn EVA cord having a diameter of about 1.1 mm. This cold-drawn EVA cord is then again elongated to break and a curve was recorded (after cold drawing) at the graph of FIG. 3. The modulus at 100% elongation was about 28.9 MPa with an elongation to break of about 150% and a maximum elastic modulus of about 44 MPa at break.

Thus, embodiments of COLD-DRAWN POLYOLEFIN COPOLYMER CORD FOR EARPLUG are disclosed.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof. The disclosed embodiments are presented for purposes of illustration and not limitation.

What is claimed is:

1. A method comprising:
uniaxially stretching a cord formed of copolymer comprising ethylene segments and vinyl acetate segments at room temperature to form a cold drawn cord, the cold drawn cord having an elongation to break of 250% or less; and
fixing the cold drawn cord to an earplug.

2. The method according to claim 1, wherein the cold drawn cord has an elongation to break of 200% or less.

3. The method according to claim 1, wherein the uniaxially stretching step comprises uniaxially stretching the cord at least 250%.

4. The method according to claim 1, wherein the cold drawn cord has an elastic modulus of 10 MPa or greater at 100% elongation.

5. The method according to claim 1, wherein the cold drawn cord has an elastic modulus of 20 MPa or greater at 100% elongation.

6. The method according to claim 1, wherein the cold drawn cord has an elastic modulus of 7 MPa or less at 100% elongation.

7. The method according to claim 1, wherein the uniaxially stretching step comprises uniaxially stretching the cord having an initial diameter to a cold drawn cord having a cold drawn diameter in a range from 40% to 80% of the initial diameter.

8. The method according to claim 1, wherein cold drawn cord has a uniform diameter in a range from 0.08 to 1.6 mm.

9. The method according to claim 1, further comprising fixing the cold drawn cord to a second earplug.

10. The method according to claim 1, wherein the fixing step comprises fixing the cold drawn cord to a portion of the earplug formed of polypropylene.

11. The method according to claim 1, wherein the copolymer comprises from 80 to 70% wt ethylene segments and from 20 to 30 wt % vinyl acetate segments.

* * * * *

UNITED STATES PATENT AND TRADEMARK OFFICE
CERTIFICATE OF CORRECTION

PATENT NO. : 11,076,995 B2  
APPLICATION NO. : 16/643153  
DATED : August 3, 2021  
INVENTOR(S) : Brown et al.

Page 1 of 1

It is certified that error appears in the above-identified patent and that said Letters Patent is hereby corrected as shown below:

In the Claims

Column 8

Line 54 (approx.), In Claim 8, before "cold drawn" insert -- the --.

Line 55 (approx.), In Claim 8, after "0.08" insert -- mm --, therefor.

Column 11

Line 62 (approx.), In Claim 11, delete "80 to 70% wt" and insert -- 80wt% to 70wt% --, therefor.

Line 63 (approx.), In Claim 11, delete "20 to 30 wt %" and insert -- 20wt% to 30wt% --, therefor.

Signed and Sealed this  
Eighth Day of March, 2022

Drew Hirshfeld  
*Performing the Functions and Duties of the  
Under Secretary of Commerce for Intellectual Property and  
Director of the United States Patent and Trademark Office*